United States Patent
Snyder et al.

[11] Patent Number: 5,174,971
[45] Date of Patent: * Dec. 29, 1992

[54] CONTINUOUS ANION EXCHANGE CHROMATOGRAPHY FOR THE SEPARATION OF ZIRCONIUM ISOTOPES

[75] Inventors: Thomas S. Snyder, Oakmont, Pa.; Michael C. Skriba, Newport Beach, Calif.; Edward J. Lahoda, Edgewood Borough, Pa.; Ernest D. Lee, Ogden, Utah

[73] Assignee: Westinghouse Electric Corp., Pittsburgh, Pa.

[*] Notice: The portion of the term of this patent subsequent to Mar. 4, 2009 has been disclaimed.

[21] Appl. No.: 597,948

[22] Filed: Oct. 10, 1990

[51] Int. Cl.⁵ .................. B01D 15/08; C22B 34/14
[52] U.S. Cl. ......................... 423/70; 423/69; 423/73; 423/2; 423/DIG. 7; 210/656; 75/612
[58] Field of Search .......... 423/70, 73, 76, 2, DIG. 7, 423/69, 74; 75/612; 210/656

[56] References Cited

U.S. PATENT DOCUMENTS 4,360,501 11/1982 Bir et al. ..................... 423/2
5,023,061 6/1991 Snyder et al. ............... 423/70
5,024,749 6/1991 Snyder et al. ............... 204/299 R

OTHER PUBLICATIONS

Journal of Chromatography, 325 (1985) 195-206 Kogure et al.
Journal of Chromatography, 259 (1983) 480-486 Kogure et al.

*Primary Examiner*—Theodore Morris
*Assistant Examiner*—Edward Squillante

[57] ABSTRACT

The thermal neutron capture cross-section of zirconium may be altered by altering its natural isotope distribution through a steady state chromatographic separation of these isotopes using an anion exchange resin as the stationary phase of the chromatographic column. Zirconium is dissolved in a very strong acid which causes the formation of a zirconium anion, such as the $ZrOCl_4^{-2}$ anion formed in six normal hydrochloric acid, and eluted off the column with a weaker acid. Distinct elution volumes representative of each isotope are collected. In a preferred embodiment, the process also separates the zirconium from hafnium and the other impurities normally present in the product obtained by chlorinating zircon sand and utilizes a continuous annular chromatograph.

25 Claims, 5 Drawing Sheets

CONTINUOUS ANION EXCHANGE CHROMATOGRAPHY FOR THE SEPARATION OF ZIRCONIUM ISOTOPES

FIELD OF THE INVENTION

The present invention is concerned with the chromatographic processing of zirconium to minimize its thermal neutron capture cross-section by altering its natural isotope distribution thus enhancing its utility as a fuel rod cladding material for nuclear reactors. It is also concerned with chromatographic processing of hafnium to separate it from zirconium and to maximize its thermal neutron capture cross-section by altering its natural isotope distribution thus enhancing its utility as a nuclear reactor control rod material.

BACKGROUND OF THE INVENTION

Zirconium metal has historically been a material of construction, in particular cladding for fuel rods, for nuclear reactors, and there has been a continuing interest in reducing its tendency to adsorb thermal neutrons. The more transparent the internal materials of construction of a nuclear reactor are to such thermal neutrons the more efficiently the reactor will function since a certain number of these neutrons are necessary to sustain the nuclear reaction and their production must compensate for the adsorption by the internal materials of construction. Early efforts were directed to separating zirconium from hafnium. The two elements occur together naturally but the hafnium has a substantially larger capture section for thermal neutrons. Such efforts involved both chromatographic techniques using an ion exchange resin and various solvent extraction techniques.

More recent efforts have been directed to isolating a zirconium isotope with either a particularly high or a particularly low cross section to thermal neutrons. This allows the production of a zirconium with a lower average cross section than one composed of the naturally occurring isotope distribution. These efforts at isotope separation have generally involved some type of solvent extraction. These separation techniques are generally only able to separate one isotope at a time. Thus they do not provide a means for simultaneously isolating the zirconium 90 and 94 isotopes which are recognized as having particularly small cross sections (one source lists them as 0.055 and 0.031 Barns, respectively, as compared to 0.567 Barns for zirconium 91 and 0.1430 for zirconium 92).

Hafnium metal, on the other hand, has historically been a material of construction for nuclear reactor control rods. In such applications, it serves its function by adsorbing thermal neutrons. However, some isotopes of hafnium are much more efficient at neutron capture because of their much greater capture cross-sections. Thus, a technique which could simultaneously isolate the high cross-section hafnium 174 and 177 isotopes (which one source reports as having cross sections of 1500 and 380 Barns, respectively, compared to values of between 14 and 75 for the remaining four isotopes) would be of significant benefit.

Recent proposals have been made that the isotopes of zirconium could be separated in an economically practical manner by the use of traditional chromatography utilizing various cation exchange resins as the stationary phase and either aqueous or non-aqueous eluants. In these procedures, however, it is difficult to effect a good separation due to problems associated with controlling the elution of the product peaks. In addition, this inherently batch approach is both expensive to build and difficult to control.

It is an object of the present invention to provide a process for simultaneously isolating both zirconium 90 and zirconium 94, which are the isotopes which both are fairly abundant and have low thermal neutron capture cross sections. It is a further object of the present invention to provide a more efficient process than solvent extraction by utilizing a chromatographic technique. It is yet another object of the present invention to provide a continuous technique for separating the isotopes of zirconium utilizing a continuously operating chromatographic technique. It is a further object to provide a technique for simultaneously isolating hafnium 174 and hafnium 177, which are the isotopes with the greatest thermal neutron capture cross-sections. It is an additional object to provide a process to separate zirconium from hafnium and in the same operation to separate the isotopes of zirconium, particularly zirconium 90 and 94, into distinct product fractions.

SUMMARY OF THE INVENTION

A process for the partial or complete separation of the isotopes of zirconium using chromatography has been developed in which an anion exchange resin is the stationary phase, an aqueous solution of anions based on a mixture of zirconium isotopes is the feed, and an aqueous acid solution is the mobile phase. The process involves the mobile phase eluting the zirconium isotopic solute, under conditions such that each of the various naturally occurring isotopes of zirconium is primarily eluted in an elution volume distinct from the elution volumes of the other isotopes. In a preferred embodiment the conditions are such that at least one of the elution volumes contains essentially only one isotope of zirconium. The process is preferably conducted in a steady state, continuous manner, and it is particularly preferred to conduct it in a continuous annular chromatograph (CAC).

A particular preferred embodiment involves feeding an aqueous solution of a zirconium anion such as $ZrOCl_4^{-2}$ to a continuous annular chromatograph with a stationary phase which comprises an anion exchange resin. The mobile phase for the elution is preferably aqueous hydrochloric acid.

Another feature is to use a crude feed stock obtained from the hydrolysis of the chlorination of zircon sand and to generate distinct product fractions for each of the hafnium, the heavy and transition metal contaminants and the radiochemical contaminants such as thorium and uranium.

An additional preferred feature is to utilize chromatographic conditions appropriate to generate distinct elution volumes for each isotope of hafnium either in the same chromatograph as is used in effect the hafnium zirconium separation or, preferably in a downstream chromatograph which utilizes the hafnium product fraction from the first chromatograph as a feedstream.

DETAILED DESCRIPTION OF THE INVENTION

Figure 1:
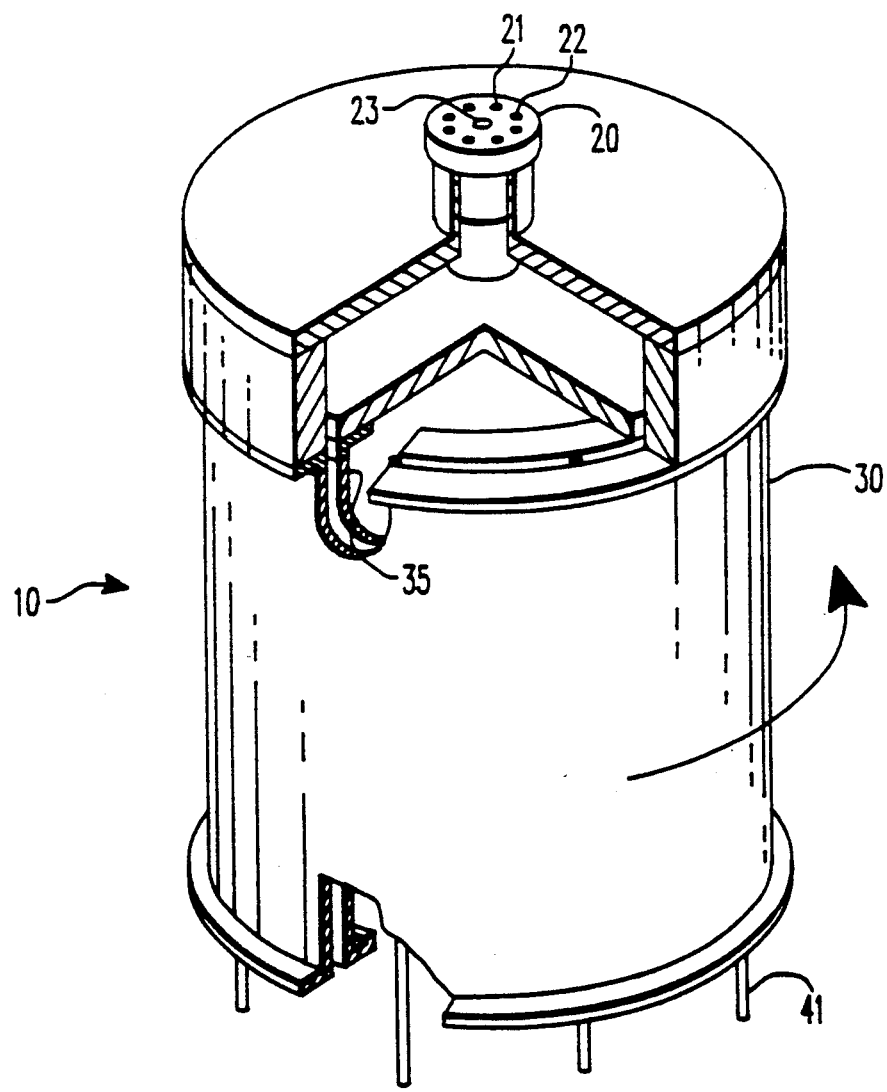
FIG. 1 is a perspective view of a continuous annular chromatograph (CAC) with a portion in section to illustrate the annular construction.
Figure 2:
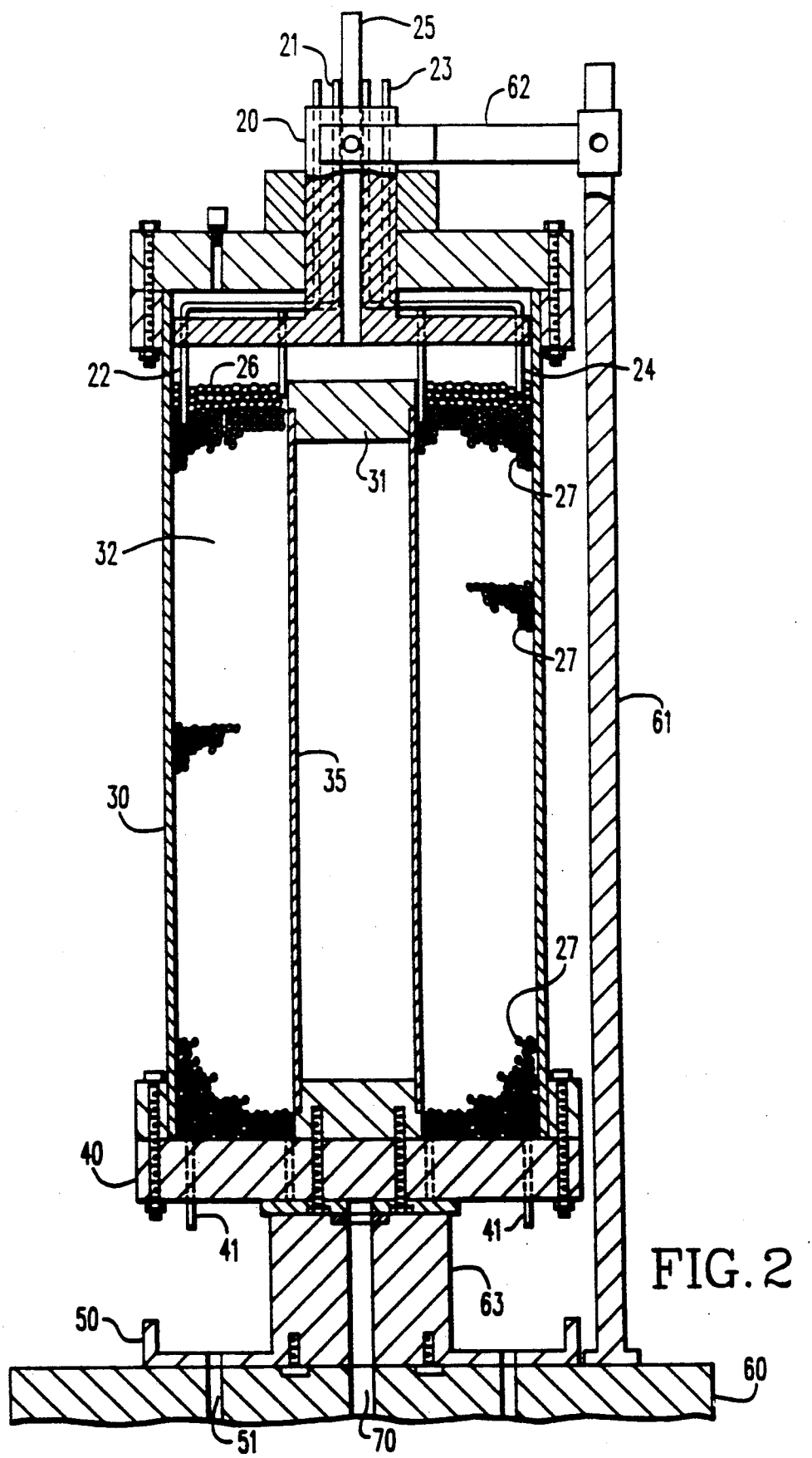
FIG. 2 is a horizontal sectional view of the CAC along a diameter of the concentric circles defining the annulus.
Figure 3:
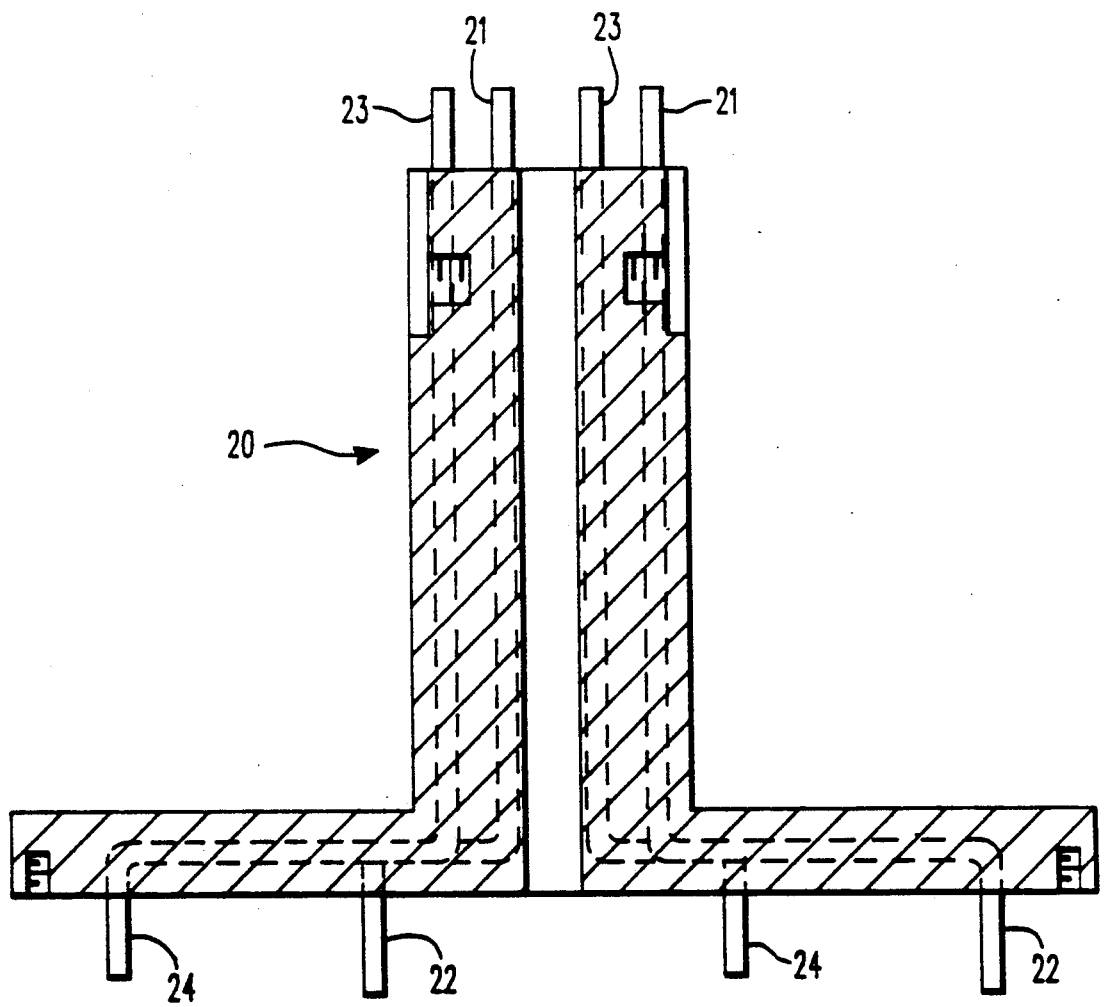
FIG. 3 is an enlarged horizontal sectional view of a part of the top portion of the CAC.
Figure 4:
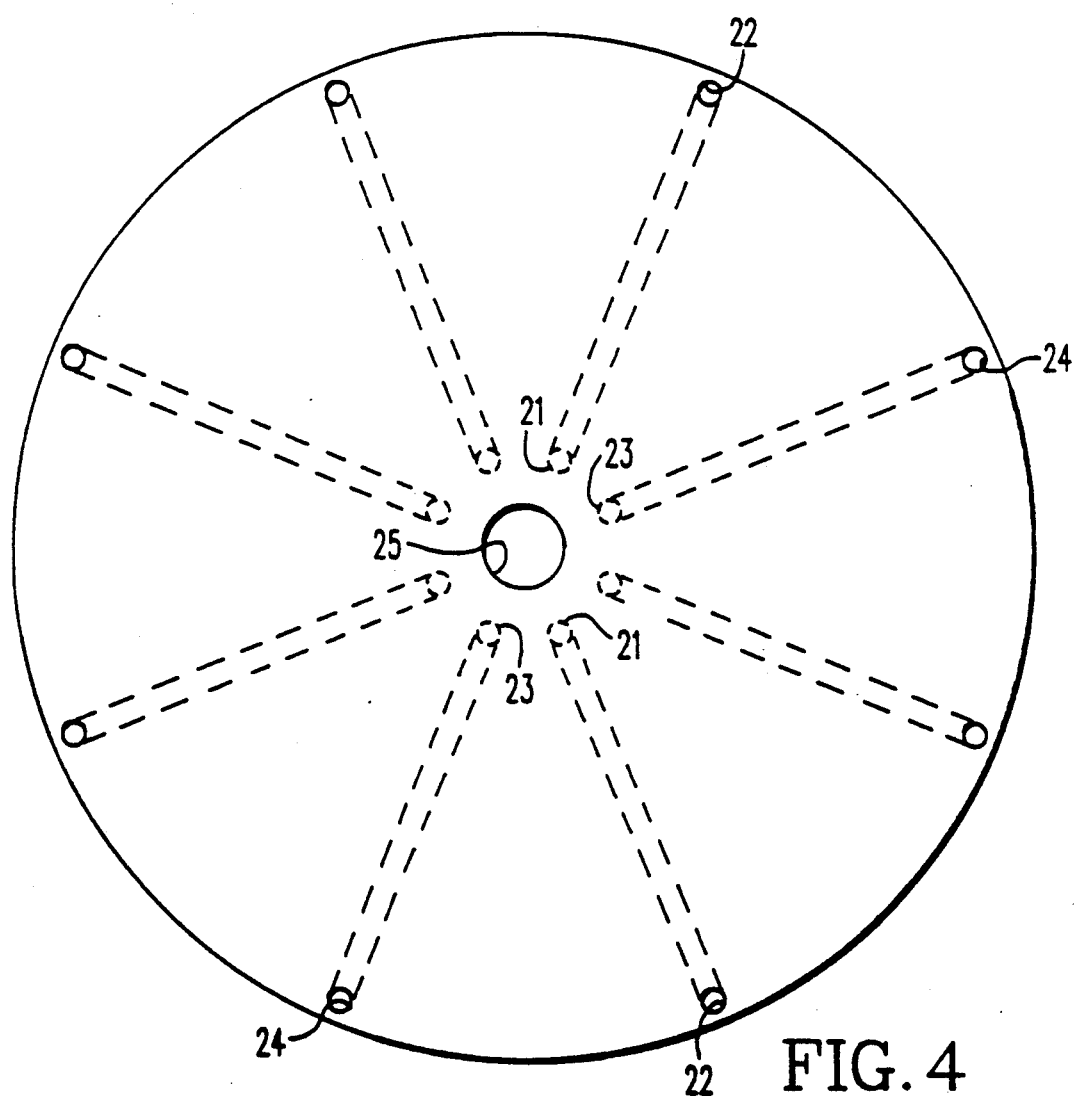
FIG. 4 is a plan view of the bottom of the item shown in FIG. 3.

The stationary phase can be any anion exchange resin with an affinity for zirconium anions. Typically, this means $ZrOCl_4^{-2}$ anions in very strong aqueous acid solutions. It is preferred that the anion exchange resin display a strong affinity for the zirconium anion in the feedstream. Particularly preferred anion exchange resins are those based on ammonium groups derived from primary and tertiary amines and the quarternary ammonium groups. Especially preferred groups are those derived from tricapryl methyl ammonium chloride, tri-n-octyl amine and primary amine.

It is also preferred that the stationary phase have a high ionic capacity per unit volume. Capacities in excess of about 0.05 milliequivalents per milliliter are particularly preferred with capacities in excess of about 0.5 milliequivalents per milliliter (or about 11 kilograms of $CaCO_3$ per $ft^3$ in U.S. commercial terms) being especially preferred. These ratings are based upon resins with bead sizes in the 500 micron range and are based on the ability to bind free acid. The smaller bead size preferred by the present invention will yield a more surface area per unit volume and consequently a higher actual capacity. On the other hand, the affinity of the resin for zirconium anions may differ from its affinity for free acid anions such as the chloride ion. The ultimate criterion is simply whether the resin can yield a reasonable separation factor, $\alpha$, under practical chromatography conditions. However, the higher the general ionic capacity of a resin, the more readily it can be adapted for use in the present invention. The Amberlite IRA series of anion exchange resins from Rohm and Haas Company fall within this particular class of preferred stationary phases with IRA 400 being particularly preferred.

It is also preferred that the stationary phase comprise a narrow monodisperse distribution of spherical particles with a small average particle size. Deviations in particle size make it more difficult to get efficient separation. Thus, a polydisperse particle size distribution will require a longer column length and result in more dilute product fractions because a larger range of eluant volumes will contain desired product. The separation efficiency can also be enhanced by lowering the particle size range of a monodisperse distribution. A small particle size is preferred because the exchange reaction is a phenomenum which occurs at the surface of the resin beads of the stationary phase. Thus, separation efficiency is enhanced by maximizing the surface to volume ratio of these resin beads. However, this needs to be balanced by the effect which decreasing the particle size has on the permeability of the stationary phase. In general, an average particle size between about 125 and 25 microns is preferred with a particle size between about 25 and 100 microns being especially preferred. A particle size of ten microns or less is optimum for separation efficiency but may pose problems of insufficient permeability for economically desired flow rates and problems of how to retain the beads in the column.

The resin beads are preferably divinyl benzene crosslinked styrene or a crosslinked acrylic resin. In any case, the resin beads making up the anion exchange resin must be stable to the very strong acid concentrations, such as 6N hydrochloric acid, used to create zirconium anions.

The feed phase may be any convenient solution of zirconium anions formed from a mixture of zirconium isotopes. The isotope mixture may be that which occurs in nature or it may be a partially refined mixture obtained from a preliminary refinement process. It may also contain the hafnium and heavy metal and radiochemical contaminants found in the commercial zirconium tetrachloride obtained from the chlorination of zircon sand, i.e., the tetrachloride obtained by chlorination in the presence of coke at about 1000° C. followed by separation from the resulting silicon tetrachloride by differential condensation.

A solution of zirconium anions may conveniently be obtained by dissolving zirconium tetrachloride in a very strong aqueous acid. Sulfuric acid, perchloric acid and more particularly hydrochloric acid at about six normal or greater are preferred. A very acid condition is typically required to generate a zirconium based anion such as $ZrOCl_4^{-2}$ for concentrated hydrochloric acid. It is preferred to convert substantially all the zirconium present to anionic form. Any zirconium not so converted will not interact with the active groups of the stationary phase and undergo isotopic separation. Furthermore, unconverted zirconium will probably end up in the same elution volumes as the heavy and transition metal contaminants which do not interact with the stationary phase.

It is preferred that the feed phase have a concentration of zirconium as high as is compatible with solubility under the anticipated operating conditions. The natural consequence of chromatographic separation is a dilution of the concentration of the products being separated into product streams. Therefore, the overall efficiency of the process and particularly a minimization of the efforts needed to recover the desired products from the product streams is best served by using as high a concentration as possible without creating an undue risk that zirconium will precipitate out during the course of the process. It is preferred to use a zirconium concentration in excess of about 0.01 molar. At 25° C., the solubility in 6N HCl is estimated to lie between about 0.04 and 0.07 molar.

The mobile phase may be an aqueous acid at a strength somewhat lower than that of the feed phase. Sulfuric acid or especially hydrochloric acid are preferred. Preferably, the mobile phase has an acid concentration between about 2 and 5 normal when the feed has an acid strength of about 6 normal or greater. The precise acid strength needed will depend upon the nature of the exchange resin's active groups and the identity of the eluant acid. It is possible to use water as the eluant since it will form a more dilute solution of the feed phase acid as it passes down the column.

In a preferred embodiment, the column height, stationary phase and elution conditions are also matched to effect a separation of hafnium isotopes into distinct product fractions. In an alternative embodiment, the hafnium product stream is fed to a second chromatographic column which separates its isotopes into distinct product fractions.

The effective column height should be sufficient to allow significant resolution of the various isotopes of the element of interest, hafnium or zirconium, into distinct product fractions. The resolution is preferably sufficient to yield an isotope purity in excess of about 90 percent, more preferably at least about 98 percent. It is preferred that this resolution be effected in a single pass through the column. The effective column height needed for a given resolution can be estimated from an application of the Kremser-Brown-Sounders equation to empirical data on the separation capacity of a given stationary phase, mobile phase, eluant and flow conditions.

An inherent result of a resolution of the isotopes of zirconium is an efficient separation of hafnium from zirconium. A process sufficiently sensitive to separate isotopes of zirconium will readily affect a separation of hafnium. It is generally expected that any hafnium present in the feed phase will elute earlier than any of the isotopes of zirconium.

Another inherent result of this isotopic resolution is the efficient separation of the heavy and transition metal contaminants and radiochemical contaminants from not only the zirconium and hafnium product fractions but from each other. The heavy and transition metal contaminants do not typically form anionic complexes and so just wash through the chromatographic column while radiochemical contaminants such as thorium and uranium do form such complexes and need to be eluted off the column.

A separation factor, $\alpha$, is used to define the ability to separate various isotopes. This factor is itself defined by the following formula for the binary case:

$$\alpha = \frac{y/(1-y)}{x/(1-x)} \quad (1)$$

wherein y is the molar concentrations of the desired isotope in the product faction rich in that isotope and x is the molar concentration of this same isotope in the tails fraction. Approximate calculations can be performed by selecting one isotopic fraction as the product, and defining the tails fraction as the composite of the other product fractions. Thus, if a product fraction is obtained in which 98% of the zirconium is zirconium 90 and if in the composite of all the other product fractions together only 2% of the zirconium is zirconium 90, the $\alpha$ defining this separation would be $$\frac{0.98/(1-0.98)}{0.02/(1-0.02)} = 2401$$

Separation factors, $\alpha$, for isotopic separations are conveniently evaluated on 25 to 100 cm columns with a 25 cm length being preferred. For such columns $\alpha$ values for the desired isotope, for instance, zirconium 90, on the preferred stationary phases with the preferred eluants are greater than about 1.05, preferably greater than about 1.085.

The effective column length required for any desired degree of purification is then determined from this data. For instance, if a 25 cm test column yields a separation factor, $\alpha$, of 1.085, this can be used as the separation factor for a theoretical stage, $\alpha_s$, in applying the Kremser-Brown-Sounders equation in estimating the number of theoretical stages, N, required. This formula can be used in the form:

$$N = \frac{\ln \alpha_T}{\ln \alpha_S}$$

For the case being discussed this yields the following result:

$$N = \frac{\ln 2401}{\ln 1.085} = 95.4$$

Thus, 95.4 theoretical stages of 25 cm each are required which implies an effective column length of about 24M.

The following table shows projected column length as a function of $\alpha$ and desired product purity. It is based on the assumption that the Kremser-Brown Saunders equation holds in the Underwood-Fenske form assuming the binary mixture approximation:

| | 98% Purity | | 95% Purity | |
|---|---|---|---|---|
| $\alpha$ for 0.25M Test Column | Number of Stages | Total Column Length (M) | Number of Stages | Total Column Length (M) |
| 1.001 | 7830 | 1960 | 4970 | 1744 |
| 1.01 | 786 | 200 | 500 | 175 |
| 1.03 | 265 | 66 | 168 | 42 |
| 1.09 | 102 | 26 | 65 | 16 |
| 1.1 | 82 | 21 | 52 | 13 |

The effective column height can be vertical but it may have other orientations. What is important is the effective path over which the mobile phase travels.

It is preferred that the path be provided in such a way that the chromatographic separation can be operated continuously. There is no convenient technique currently available for instantaneously sensing the concentration of any given isotope. Thus, there is a preference for a continuously operating procedure which has reached steady state so that a particular product fraction reproducibly has a certain isotope distribution. If the chromatographic separation is effected in a discontinuous or batch manner random variations between runs may make it difficult to reproducibly collect product fractions with the same isotope distributions from run to run. For instance, if a single vertical column is loaded in a batch manner the elution time of the product fraction rich in a particular isotope may vary from run to run due to random variables difficult to control such as feed concentration fluctuations, etc.

A particularly preferred continuously operating chromatograph is the continuous annular chromatograph (CAC). This device was developed by Oak Ridge National Laboratory and comprises an annular stationary phase which is rotated about the axis of the annulus. The annulus is provided by packing the stationary phase material, such as resin beads, between two concentric cylinders of differing diameters with coincident vertical axes. A feed port is provided at a given angular position and one or more eluant ports are provided at some angular offset from the feed port. It is preferred to place a layer of glass beads above the stationary phase, and to feed the eluant to the glass beads while feeding the zirconium feedstock directly to the top of the stationary phase. This should prevent any undesired mixing effects.

This device is provided with a number of product ports set at a number of angular positions which can be set arbitrarily to accommodate a particular set of operating condition. Each product port collects an elution volume which has had a particular residence time on the column. The stationary phase is typically rotated at a constant speed so that any vertical segment of the annular bed is above a particular fixed product collection port at a given time after this segment has been loaded with feedstock and eluant. Thus, each product collection port has an angular position which corresponds to a particular elution time for a particular rate of rotation of the stationary phase and for a particular flow rate through the stationary phase.

The flow rate through the stationary phase is controlled by the pressure drop across the effective height of the stationary phase and the physical characteristics of the stationary phase, i.e., particle size and packing void volume. This pressure drop may be provided by the hydrostatic head of the feedstock and eluant but it is preferably provided by pressurizing the device. The pressure required to achieve a particular flow rate is governed by the nature of the stationary phase; the smaller the average particle of the resin beads making up the stationary phase the larger the pressure drop required to obtain a particular flow rate over a particular effective height. However, the separation factor for any given theoretical stage is improved as the average particle size of the resin beads is decreased. Thus, the effective height needed to effect a given degree of separation is decreased as the separation capacity of a unit length (or theoretical stage height) is increased by decreasing the average particle size of the resin beads.

The flow rate across the effective height of the stationary phase and the rotational speed of the stationary phase should be coordinated such that a particular product fraction always elutes at the same angular position and thus is always delivered to the same product collection port.

The chromatograph may be configured to separate just the isotopes of zirconium or to also separate the isotopes of hafnium. In the former case, all the hafnium will be collected as a single product fraction although this may involve combining the output of a number of product ports. In the latter case, it will be necessary to design the column to provide an adequate separation factor, $\alpha$, and a sufficient column length to effect isotopic separation of both zirconium and hafnium. Depending on the nature of the active groups of the stationary phase and the feedstock carrier, the $\alpha$ for one element may be less than for the other thus requiring a longer column length.

If the feed also contains the heavy and transition metal contaminants and radiochemical contaminants typically found in the hydrolyzed chlorination product obtained from zircon sand, it will be necessary to assign product ports to these contaminants. The former class of contaminants are not expected to interact with the anion exchange resin of the stationary phase and are consequently expected to pass straight down the column. They will, therefore, be contained in the first elution volume which, in fact, will emerge from the column before any of the true eluant. Thus, these contaminants will be collected at essentially the same concentration as they were in the feed. On the other hand, the latter class of contaminants are expected to form anionic complexes in the feed and interact with the stationary phase. Therefore, the heavy and transition metal contaminants will be effectively separated from the radiochemical contaminants thus making the disposal of these two classes of waste less burdensome (Each class has its own different requirements for disposal).

On the other hand, the feed may be essentially pure zirconium or a mixture of a zirconium and hafnium. One convenient way of obtaining such a purified feed is to initially separate the impurities in one chromatograph and to effect isotopic separation in further chromatographic columns. It is preferred to effect the zirconium and hafnium isotopic separations in separate chromatographs, thus providing maximum flexibility with regard to eluants phases, column design and operating conditions. It is further preferred to effect elemental separation in a first chromatograph and then effect isotopic separations in subsequent chromatographs.

In one preferred embodiment, a feed containing the product obtained by hydrolyzing the zirconium fraction of the chlorination of zircon sand over coke is fed to a first continuous annular chromatograph to effect elemental separation. It is generally anticipated that the hafnium will be present in an earlier elution volume than this zirconium. The zirconium product fraction from the chromatograph is then fed to a second such chromatograph to effect isotope separation. In a particularly preferred embodiment, the hafnium product fraction from the first chromatograph is fed to its own chromatograph to effect isotope separation.

It is preferred that the isotope separation chromatographs be operated in a displacement mode wherein no more than about 5 percent, more preferably no more than about 1 percent of the effective column height, is loaded with feed solution before elution is initiated. This is conveniently effected by using a feed solution which is unable to release the anions of interest from ionic bonding with the anion exchange resin and loading no more than about 5 percent, preferably about 1 percent of the effective height, before adding an eluant of suitable strength to cause these anions to migrate down the column at a reasonable rate. In the continuous annular chromatograph this end is achieved by coordinating the angular displacement between the feed port and the eluant port and the speed of rotation of the annular bed so that the time interval between loading and elution is just sufficient for the desired degree of penetration. The relationship between the time for loading and the depth of penetration is in turn governed by the flow rate through the annular bed.

The displacement may be effected by either an isocratic or a gradient supply of eluant. In the former case, the eluant can simply be supplied from a single port while in the latter case, several ports at successively greater angular displacements from the feed port are utilized. In the gradient mode, elution under the influence of the initial eluant is permitted to proceed until some separation of the isotopes of interest has been effected and then a more effective eluant is supplied. This increases the migration speed of these isotopes down the column and minimizes the range of elution volumes or times over which a given component or product fraction will exit the column or, in other words, this procedure minimizes the band spreading.

Decreasing the elution volumes by gradient elution or by other means increases the concentration of the product, e.g., the zirconium isotope, in the product fraction.

The flow rate down the column is governed by the pressure drop from the top to the bottom of the column and the nature of the stationary phase. The smaller the average particle size of the resin beads making up the stationary phase the higher the pressure drop required to obtain a given flow rate. This relationship is also effected by the particle size distribution of these resin beads. There is, however, a maximum attainable flow rate for any given anion exchange resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 2 and 80, more preferably between about 3 and 20 gallons per minute per square foot of cross sectional area (between about $1.36 \times 10^{-3}$ and $5.43 \times 10^{-2}$ m$^3$/sec, more preferably between about $2.04 \times 10^{-3}$ and $1.36 \times 10^{-2}$ m$^3$/sec per square meter of cross sectional area). There is a relationship between the achievable flow rates and the effective column height needed for a given degree of purity. For a given system of stationary phase and eluant, the theoretical stage separation factor, $\alpha_S$, of the stationary phase for any isotope of interest will increase as the average particle size of the resin beads of the stationary phase decrease. However, as this particle size decreases so does the flow capacity of the stationary phase. Thus, there is an inverse relationship between $\alpha_S$ and the flow capacity. Thus, a higher flow rate will require a greater effective column height to achieve the same degree of separation or product fraction purity.

Furthermore, there is the additional constraint that the pressure required to achieve the desired flow rate not exceed the capability of available pumps, seals and feed tubing. The required pressure is a function of both the pressure drop needed per unit of effective height and the total effective height required for the desired degree of separation. Thus, as the flow capacity of the stationary phase is increased by a change in its physical configuration and consequently its theoretical stage separation factor, $\alpha_S$, is decreased, the required effective height and the required overall pressure drop are both increased. On the other hand, as the theoretical stage separation factor, $\alpha_S$, is increased by a change in the resin bead size distribution and consequently the flow capacity of the stationary phase is decreased, the pressure drop for a given effective height is increased. A total column pressure drop of less than about 2758 kPa (400 psi) more especially between about 345 and 1042 kPa (50 and 150 psi) is preferred.

Thus, to obtain a system with a commercially practical capacity, it is necessary to use a stationary phase which will simultaneously display both a reasonable theoretical stage factor, $\alpha_S$, and a reasonable flow rate per unit of effective height with a reasonable pressure drop. This can be achieved by an appropriate selection of both the ionic capacity of the stationary phase anion exchange resin and the eluant.

In a preferred mode several product collection ports are used to collect a particular product fraction. This is accomplished by closely spacing these collection ports so that they more than span the angular range of rotation that corresponds to the elution time interval of that particular fraction but do not extend to angular positions at which any significant portion of any other product fraction is expected to elute. Of course, this requires that the elution time intervals of different product fractions do not substantially overlap. This arrangement tends to insure that minor fluctuations in the steady state elution behaviour which would cause a slight advancement or retardation of the elution time of the desired product fraction will not result in any loss of this fraction.

Of course, if the elemental separation is effected in one column and the isotopic separation or separations in another, the operating conditions in each column may be optimized with regard to the functions of that column. For instance, the ratio of zirconium to hafnium in the hydrolyzed chlorinated product from zircon sand is rather large, typically 50:1, so that the feed rate to the chromatograph separating the isotopes of hafnium will be much smaller and therefore, the flow rate through this chromatograph may be smaller. Thus, the column cross section can be smaller. In addition, the eluant can be selected to give the optimum separation factor, $\alpha$, for hafnium.

A particular preferred device for use in practicing the present invention is illustrated in FIGS. 1 through 5. The continuous annular chromatograph 10 illustrated in FIG. 1 comprises two concentric cylinders 30 and 35 which define the annular space 32 seen in FIG. 2. Atop this annular space 32 is a distributor plate 20. Feed pipes or channels 21 and 23 run through the distributor plate 20 and terminate in feed nozzles 22 and 24, respectively. The feed nozzles 22 are intended to supply the feed phase to the exchange resin beads 27 which are packed in the annular space 32. For ease of illustration, these beads are shown as only partially filling the annular space 32. On the other hand, the feed nozzles 24 are intended to feed the eluant to the layer of glass beads 26 which sits atop the exchange resin beads 27. Thus the feed nozzles 24 are somewhat shorter than the feed nozzles 22. This feed arrangement serves to avoid any back mixing of the feed phase.

The central cavity defined by the inner cylinder 35 is sealed by a cap 31 so that pipe or channel 25 can be used to apply pressure to the annular bed of resin beads 22.

Figure 5:
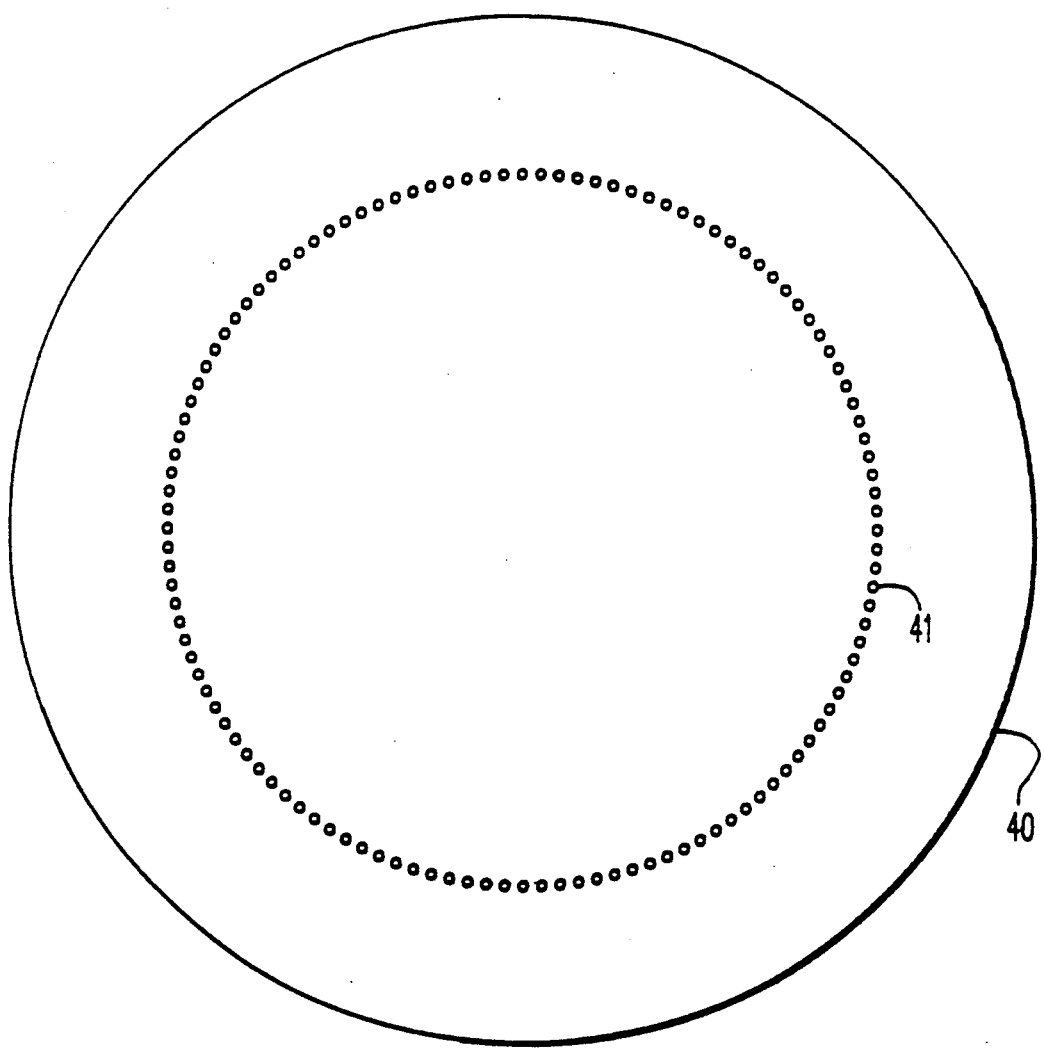
FIG. 5 is a plan view of the bottom of the CAC.

The bottom of the annular space 32 is defined by a product plate 40. As seen in FIG. 5, a large number of product delivery channels or pipes 41 pass through this plate. This allows the collection of a variety of product fractions and also facilitates adjustments to the operating conditions to allow product collection at various angular displacements.

The distributor plate 20 is held in a fixed position above the annular space 32 by a bracket 62 which is turn connected to a support rod 61 which is affixed to a base plate 60. Also affixed to this base plate 60 is a support column 63 on which the product plate 40 rotatably rests. A shaft 70 passes through this support column 63 and base plate 60 and connects the product plate 40 to a motivating means not shown. Also affixed to the base plate 60 is an annular collection trough 50 which can be subdivided into any number of convenient segments, each with its own exit port 51.

The continuous annular chromatograph 10 is operated by rotating the annular space 32 packed with the resin beads 27 beneath the fixed distributor plate 20 and its associated feed nozzles 22 and 24. The rotational force is supplied by the shaft 70.

We claim:

1. A process for reducing the thermal neutron capture cross-section of zirconium by increasing the concentration of the low cross-section isotopes and decreasing the concentration of the high cross-section isotopes which comprises subjecting a solution of zirconium anions with a higher than desired distribution of high cross-section isotopes to continuous steady state chromatography utilizing an anion exchange resin as the stationary phase, collecting at least two product fractions, one enriched in zirconium 90 and the other enriched in zirconium 94, and combining them to yield a zirconium with a lower cross-section than the starting zirconium.

2. The process of claim 1 wherein the concentration of the zirconium 90 in its product fraction is in excess of 90 mol percent.

3. The process of claim 1 wherein the continuous steady state chromatography is effected in a continuous annular chromatograph.

4. The process of claim 1 wherein the zirconium anions are hydrolyzed chlorides.

5. The process of claim 1 wherein said solution includes an eluant formed from an aqueous solution of a strong mineral acid.

6. The process of claim 1 wherein said solution includes an eluant formed from between a 1 and 10 normal aqueous solution of hydrochloric acid.

7. The process of claim 5 wherein the anion exchange resin has a capacity of at least about 0.05 milliequivalents per milliliter at a particle size of 500 microns.

8. The process of claim 7 wherein the anion exchange resin is composed of a monodisperse distribution of spherical beads with an average particle size of between about twenty five and 100 microns.

9. The process of claim 1 wherein the separation factor, $\alpha$, for a theoretical stage of 25 cm in height for zirconium 90 is at least about 1.05.

10. The process of claim 1 in which the solution of zirconium anions also contains hafnium anions and the chromatography essentially completely separates the hafnium anions from the zirconium product fractions.

11. The process of claim 1 wherein the active groups of the anion exchange resin are derived from the group consisting of primary amines, tertiary amines, quaternary ammonium groups and combinations thereof.

12. A process for recovering a zirconium fraction with an enhanced concentration of the 90 and 94 isotopes comprising subjecting a solution of zirconium anions with a natural isotope distribution to continuous steady state chromatography utilizing an anion exchange resin as the stationary phase, collecting at least two product fractions, each enriched in one of these isotopes, and combining these two fractions.

13. A commercial process for obtaining zirconium with a reduced thermal neutron cross-section by increasing the concentration of the low cross-section isotopes and decreasing the concentration of the high cross-section isotopes which comprises 1) preparing an aqueous solution of zirconium oxychloride by hydrolyzing zirconium tetrachloride with a natural isotope distribution in water to a solution strength of at least about one molar,
2) raising the acidity of the solution to a value sufficient to assure that the zirconium atoms present become part of oxychloride anions,
3) subjecting this solution to continuous steady state chromatography in a continuous annular chromatograph wherein
   a) the eluant is a hydrochloric acid,
   b) the stationary phase comprises an anion exchange resin which has
      i) amino nitrogen derived active groups,
      ii) a capacity of at least about 0.05 milliequivalents per milliliter measured at a 500 micron particle size,
      iii) a monodisperse particle distribution of approximately spherical beads with an average particle size of about twenty-five microns or less, and
      iv) a separation factor, $\alpha$, for zirconium 90 for a 25 cm theoretical stage of at least about 1.05 under the elution conditions, and
   c) the effective height of the stationary phase is sufficient to yield a zirconium 90 product fraction which comprises 98 mol percent of zirconium 90, and
4) collecting the two product fractions comprising mainly zirconium 90 and zirconium 94, respectively.

14. The process of claim 13 wherein the aqueous zirconium oxychloride solution also contains hafnium oxychloride and the chromatography essentially completely separates the hafnium anions from the zirconium product fractions.

15. The process of claim 13 wherein the eluant has a hydrochloric acid strength of between about 1 and 10 normal.

16. The process of claim 13 wherein the continuous annular chromatograph is operated so that the zirconium anion solution penetrates about one percent of the effective column height before the eluant is added.

17. The process of claim 16 wherein the stationary phase has a capacity of at least about 0.5 milliequivalents per milliliter measured at a particle size of 500 microns.

18. The process of claim 13 wherein the eluant is fed to the annular bed at more than one circumferential position and the hydrochloric acid concentration of the eluant is decreased at each successive feed position moving in the direction of rotation of the continuous annular chromatograph.

19. The process of claim 13 wherein the active groups of the anion exchange resin are derived from one of the groups consisting of primary amines, tertiary amines, quaternary ammonium groups and combinations thereof.

20. The process of claim 13 wherein the initial zirconium solution is obtained by dissolving the zirconium condensation fraction obtained from chlorinating zircon sand in the presence of coke.

21. The process of claim 20 wherein at least one product fraction enriched in hafnium 174 or hafnium 177 is also generated.

22. The process of claim 21 wherein the hafnium isotopic separation is effected in a different chromatograph from the one in which the zirconium isotopic separation is effected.

23. The process of claim 20 wherein elemental separation is effected in a first chromatograph and the separation of the zirconium isotopes is effected in a downstream chromatograph.

24. The process of claim 13 wherein the flow rate through the isotopic separation chromatograph is between about 2 and 80 gallons per minute per square foot of cross section traverse to the flow.

25. The process of claim 24 wherein the pressure drop across the effective height of the isotopic separation chromatograph is less than about 150 psi.

* * * * *